US012589118B2

(12) United States Patent
Winter et al.

(10) Patent No.: US 12,589,118 B2
(45) Date of Patent: Mar. 31, 2026

(54) METHOD OF PROLONGING THE LIFESPAN OF PATIENTS WITH CEREBRAL AUTOSOMAL DOMINANT ARTERIOPATHY WITH SUBCORTICAL INFARCTS AND LEUKOENCEPHALOPATHY (CADASIL) USING A CEREBROLYSIN® PREPARATION

(71) Applicant: EVER NEURO PHARMA GMBH, Unterach am Attersee (AT)

(72) Inventors: Stefan Winter, Scharfling (AT); Herbert Mössler, Mondsee (AT)

(73) Assignee: EVER NUERO PHARMA GMBH, Unterach am Attersee (AT)

( * ) Notice: Subject to any disclaimer, the term of this patent is extended or adjusted under 35 U.S.C. 154(b) by 244 days.

(21) Appl. No.: 16/642,307

(22) PCT Filed: Aug. 28, 2018

(86) PCT No.: PCT/EP2018/073106
§ 371 (c)(1),
(2) Date: Feb. 26, 2020

(87) PCT Pub. No.: WO2019/042983
PCT Pub. Date: Mar. 7, 2019

(65) Prior Publication Data
US 2020/0376040 A1      Dec. 3, 2020

(30) Foreign Application Priority Data
Aug. 28, 2017    (EP) ..................................... 17188180

(51) Int. Cl.
| | |
|---|---|
| *A61K 38/16* | (2006.01) |
| *A61K 35/30* | (2015.01) |
| *A61K 38/00* | (2006.01) |
| *A61K 38/17* | (2006.01) |
| *A61K 38/18* | (2006.01) |
| *A61P 9/10* | (2006.01) |
| *A61P 25/00* | (2006.01) |
| *A61P 25/28* | (2006.01) |
| *C07K 14/00* | (2006.01) |
| *C07K 14/475* | (2006.01) |
| *C07K 14/48* | (2006.01) |
| *A61K 9/00* | (2006.01) |
| *C07K 14/435* | (2006.01) |
| *C07K 14/46* | (2006.01) |
| *C07K 14/47* | (2006.01) |

(52) U.S. Cl.
CPC .......... *A61K 35/30* (2013.01); *A61K 38/1709* (2013.01); *A61K 38/18* (2013.01); *A61K 38/185* (2013.01); *A61P 9/10* (2018.01); *A61P 25/00* (2018.01); *A61P 25/28* (2018.01); *C07K 14/475* (2013.01); *C07K 14/48* (2013.01); *A61K 9/0019* (2013.01); *A61K 38/16*

(2013.01); *A61K 38/1703* (2013.01); *C07K 14/435* (2013.01); *C07K 14/46* (2013.01); *C07K 14/47* (2013.01)

(58) Field of Classification Search
CPC .. A61K 38/00; A61K 38/1709; A61K 38/185; A61K 38/17; A61K 38/18; C07K 14/47; C07K 14/4705; C07K 14/475; C07K 14/48; A61P 25/28; A61P 25/00; A61P 9/00; A61P 9/10
See application file for complete search history.

(56) References Cited

U.S. PATENT DOCUMENTS 8,034,778 B2 * 10/2011 Hitzl .................... C07K 5/1021
514/18.1

FOREIGN PATENT DOCUMENTS

| EP | 0452299 | 10/1991 |
|---|---|---|
| EP | 1857463 | * 11/2007 |
| JP | 2012-501967 | 11/2011 |

OTHER PUBLICATIONS

The factsheet of NCT00868283 retrieved from the NIH clinical trials website:clinicaltrials.gov/ct2/show/record/NCT00868283 on Dec. 13, 2021.*
Lundkvist et al.. Genesis. 2005;41(1):13-2.*
Dichgans, The Lancet-Neurol. 2007; 6:149-161.*
The factsheet of clinical trial No. NCT00947531 retrieved from NIH clinical trials website: clinicaltrials.gov/ct2/show/study/NCT00947531 on Dec. 13, 2021.*
Chabriat et al. The Lancet-Neurol. 2009; 8:643-653.*
Heiss et al., Stroke, 2012; 43:630-636.*
The 2020 updated of NCT00947531 retrieved from the website: clinicaltrials.gov/ct2/history/NCT00947531?V_3= View#StudyPageTop on Aug. 27, 2022.*
The meaning of "mortality" retrieved from the Merriam-Webster online dictionary website on Jun. 14, 2023.*
Chabriat et al. Lancet Neurol. 2009; 8:643-53.*
Joutel et al. Lancet 1997; 350:1511-15.*
Formichi et al. Neurol. Sci. 2013:34-553-556.*
Behrouz, et al., "What Are the Mortality Rates for Cerebral Autosomal Dominant Arteriopathy with Subcortical Infarcts and Leukoencephalopathy (CADASIL)?," Medscape.
Chen, et al., "Cerebrolysin for Vascular Dementia (Review)," Cochrane Database of Systematic Reviews, Jan. 31, 2013.
Di Donato, et al., "Cerebral Autosomal Dominant Arteriopathy with Subcortical Infarcts and Leukoencephalopathy (CADASIL) as a Model of Small Vessel Disease: Update on Clinical, Diagnostic, and Management Aspects," BMC Medicine, 15(1): 2017.
Extended European Search Report Issued in Corresponding European Patent Application No. 17188180.8, dated Feb. 1, 2018.

(Continued)

*Primary Examiner* — Chang-Yu Wang
(74) *Attorney, Agent, or Firm* — Norton Rose Fulbright US LLP

(57) ABSTRACT

Disclosed is cerebrolysin for use in reducing mortality in CADASIL (cerebral autosomal dominant arteriopathy with subcortical infarcts and leukoencephalopathy) patients.

15 Claims, 3 Drawing Sheets

(56) References Cited

OTHER PUBLICATIONS

Figure 1:
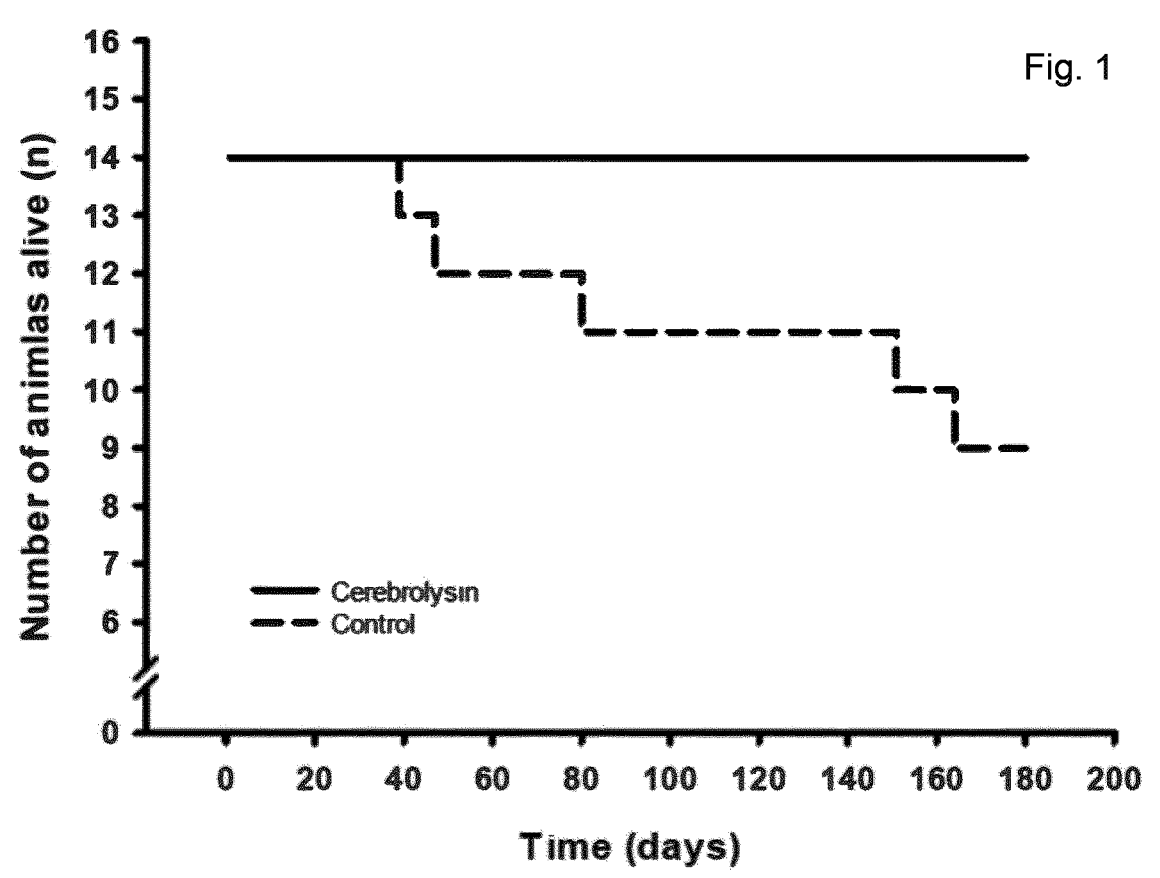

Formichi, et al., "Effects of Cerebrolysin Administration on Oxidative Stress-Induced Apoptosis in Lymphocytes from CADASIL Patients," Neurological Sciences, 34(4): 553-556, 2012.

Ghosh, et al. "Lamin A Is an Endogenous SIRT6 Activator and Promotes SIRT6-Mediated DNA Repair," Cell Reports, 13: 1396-1406, 2015.

International Search Report and Written Opinion Issued in Corresponding PCT Patent Application No. PCT/EP2018/073106, mailed Oct. 29, 2018.

Joutel, et al., "Cerebrovascular Dysfunction and Microcirculation Rarefaction Precede White Matter Lesions in a Mouse Genetic Model of Cerebral Ischemic Small Vessel Disease," Journal of Clinical Investigation, 120(2): 433-445, 2010.

Joutel, et al., "Notch3 Mutations in CADASIL, A Hereditary Adult-Onset Condition Causing Stroke and Dementia," Nature, 383: 707-710, 1996.

Rutten & Oberstein, "CADASIL Synonym: Cerebral Autosomal Dominant Arteriopathy with Subcortical Infarcts and Leukoencephalopathy," Gene Reviews, Seattle, WA: University of Washington, Seattle; 1993-2017. Retrieved Feb. 7, 2017, from https://www.ncbi.nim.nih.gov/books.NBK1600/?report=printable.

Gromova, et al., Difficult Patient 8: 25-31, 2010 (English Machine Translation).

Ayata, "CADASIL—Experimental Insights From Animal Models," Stroke 2010.

Baron-Menguy et al., "Increased Notch3 Activity Mediates Pathological Changes in Structure of Cerebral Arteries," Hypertension 2017.

Cognat et al., "Archetypal Arg169Cys Mutation in NOTCH3 Does Not Drive the Pathogenesis in Cerebral Autosomal Dominant Arteriopathy With Subcortical Infarcts and Leucoencephalopathy via a Loss-of-Function Mechanism," Stroke 2014.

Frederico et al., "The spectrum of mutations for CADASIL diagnosis," Neurol Sci vol. 26, pp. 117-124, 2005.

Ghosh et al., "Pericytes Are Involved in the Pathogenesis of Cerebral Autosomal Dominant Arteriopathy with Subcortical Infarcts and Leukoencephalopathy," Ann Neurol vol. 78, pp. 887-900, 2015.

Joutel et al. "Cerebrovascular dysfunction and microcirculation rarefaction precede white matter lesions in a mouse genetic model of cerebral ischemic small vessel disease," J Clin Invest. vol. 120, No. 2, pp. 433-445, 2010.

Joutel et al., "Notch3 mutations in CADASIL, a hereditary adult-onset condition causing stroke and dementia," Nature vol. 383, 1996.

Markus et al., "Diagnostic strategies in Cadasil," Neurology vol. 59, 2002.

Monet-Lepretre et al., "Abnormal recruitment of extracellular matrix proteins by excess Notch3$^{ECD}$: a new pathomechanism in CADASIL," Brain vol. 136, pp. 1830-1845, 2013.

Peters et al., "A Two-Year Clinical Follow-Up Study in 80 CADASIL Subjects—Progression Patterns and Implications for Clinical Trials," Stroke 2004.

Razvi et al., "Diagnostic strategies in Cadasil," Neurology vol. 60, 2019.

Rutten et al., "The NOTCH3 score: a pre-clinical CADASIL biomarker in a novel human genomic NOTCH3 transgenic mouse model with early progressive vascular NOTCH3 accumulation,"

Acta Neuropathologica Communications vol. 3, No. 89, 2015.

Tikka et al., "Congruence between NOTCH3 mutations and GOM in 131 CADASIL patients," Brain vol. 132, pp. 933-939, 2009.

Beghi et al., "European Academy of Neurology and European Federation of Neurorehabilitation Societies guideline on pharmacological support in early motor rehabilitation after acute ischaemic stroke", European Journal of Neurology, (2021), pp. 2831-2845.

Bornstein et al., "Safety and efficacy of Cerebrolysin in early post-stroke recovery: a meta-analysis of nine randomized clinical trials", Neurological Sciences (2018) 39, pp. 629-640.

Chabriat et al., "Predictors of Clinical Worsening in Cerebral Autosomal Dominant Arteriopathy With Subcortical Infarcts and Leukoencephalopathy: Prospective Cohort Study", Stroke—American Heart Association, (2016), 47:4-11. DOI: 10.1161/STROKEAHA.115.010696, pp. 4-11.

Deboer et al., "Enhanced Spontaneous Motor Recovery After Stroke in Mice Treated With Cerebrolysin", Neurorehabilitation and Neural Repair, (2021), vol. 35(6) 525- 533.

Gauthier et al., "Cerebrolysin in Mild-to-Moderate Alzheimer's Disease: A Meta-Analysis of Randomized Controlled Clinical Trials", Dement Geriatr Cogn Disord, (2015); 39: pp. 332-347.

Guekht et al., "Safety and efficacy of Cerebrolysin in motor function recovery after stroke: a meta-analysis of the CARS trials", Neurol Sci, (2017) 38, pp. 1761-1769.

Guekht et al., "Cerebrolysin in Vascular Dementia: Improvement of Clinical Outcome in a Randomized, Double-Blind, Placebo-Controlled Multicenter Trial", Journal of Stroke and Cerebrovascular Diseases, vol. 20, No. 4 (2011), pp. 310-318.

Kastberger et al., "Treatment with Cerebrolysin Prolongs Lifespan in a Mouse Model of Cerebral Autosomal Dominant Arteriopathy with Subcortical Infarcts and Leukoencephalopathy", Adv. Biology, (2023), 2300439, pp. 1-11.

Ling et al., "Clinical correlates of longitudinal MRI changes in CADASIL", Journal of Cerebral Blood Flow & Metabolism, (2019), vol. 39(7), pp. 1299-1305.

Matiytsiv et al., "Cerebrolysin® Influences in Sod- and sws-Dependent Neurodegenerative Models of Drosophila melanogaster", Biol. Stud. (2023), 17(2), pp. 3-14.

Mizuno et al., "Clinical and Genetic Aspects of CADASIL", Frontiers in Aging Neuroscience, (2020) vol. 12, Article 91, pp. 1-10.

Opherk et al., "Long-term prognosis and causes of death in CADASIL: a retrospective study in 411 patients", Brain, (2004), 127, pp. 2533-2539.

Rutten et al., "The effect of NOTCH3 pathogenic variant position on CADASIL disease severity: NOTCH3 EGFr 1-6 pathogenic variants are associated with a more severe phenotype and lower survival compared with EGFr 7-34 pathogenic variants", Genetics in Medicine, vol. 21, No. 3, (2019), pp. 676-682.

Scheid et al., "Correlation of cognitive status, MRI- and SPECT-imaging in CADASIL patients", European Journal of Neurology, (2006), 13, pp. 363-370.

Singhal et al., "The influence of genetic and cardiovascular risk factors on the CADASIL phenotype", Brain (2004), 127, pp. 2031-2038.

Zhang et al., "Cerebrolysin dose-dependently improves neurological outcome in rats after acute stroke: A prospective, randomized, blinded, and placebo-controlled study", International Journal of Stroke, (2016), 0(0), pp. 1-9.

Korczyn et al., "Vascular dementia," Journal of the Neurological Sciences vol. 322, pp. 2-10, 2012.

* cited by examiner

METHOD OF PROLONGING THE LIFESPAN OF PATIENTS WITH CEREBRAL AUTOSOMAL DOMINANT ARTERIOPATHY WITH SUBCORTICAL INFARCTS AND LEUKOENCEPHALOPATHY (CADASIL) USING A CEREBROLYSIN® PREPARATION

CROSS-REFERENCE TO RELATED APPLICATIONS

This application is a national phase application under 35 U.S.C. § 371 of International Application No. PCT/EP2018/073106 filed 28 Aug. 2018, which claims priority to European Patent Application No. 17188180.8 filed 28 Aug. 2017. The entire contents of each of the above-referenced disclosures is specifically incorporated by reference herein without disclaimer.

BACKGROUND

A. Technical Field

The present invention relates to the treatment of CADASIL.

B. Description of Related Art

CADASIL (for cerebral autosomal dominant arteriopathy with subcortical infarcts and leukoencephalopathy; or: CADASIL syndrome) causes a type of lacunar syndrome accompanied by obliviousness whose key features include recurrent sub-cortical ischaemic events and vascular dementia and which is associated with diffuse white-matter abnormalities on neuro-imaging. CADASIL is inherited in an autosomal dominant manner. Most affected individuals have an affected parent; de novo pathogenic variants appear to be rare. Each child of an affected person is at a 50% risk of inheriting the pathogenic variant and developing signs of the disease. Prenatal testing for a pregnancy at increased risk and preimplantation genetic diagnosis are possible if the pathogenic variant in the family is known; however, requests for prenatal testing of typically adult-onset disorders are uncommon. Pathological examination reveals multiple small, deep cerebral infarcts, a leukoencephalopathy, and a non-atherosclerotic, non-amyloid angiopathy involving mainly the small cerebral arteries. Severe alterations of vascular smooth-muscle cells are evident on ultrastructural analysis. The mutant gene was mapped to chromosome 19 and mutations of the human Notch3 gene were identified in CADASIL patients that cause serious disruption of this gene.

In fact, more than 95% of individuals with CADASIL have pathogenic missense variants in Notch3 (Rutten et al., in: Pagon et al. (Eds.) GENEREVIEWS® (2000; updated 2016); Seattle (Wash.): University of Washington, Seattle; 1993-2017; Joutel et al., Nature 383 (1996), 707-710). Whereas over 95% of Notch3 mutations in CADASIL patients are missense mutations, others are small in-frame deletions or splice-site mutations. Strikingly, all pathologic mutations lead to an odd number of cysteine residues within a given EGFR. The cysteine residues are believed to contribute to the structural integrity of the protein, thus additional or missing cysteine residues possibly compromise the correct protein folding. De novo mutations are rare but individual cases have been reported.

The pathologic hallmark of CADASIL is constituted by electron-dense granules in the media of arterioles, and increased Notch3 staining of the arterial wall, which can be evaluated in a skin biopsy. There is currently no treatment of proven efficacy for CADASIL. Antiplatelet treatment is frequently used, but not proven effective in CADASIL. Migraine should be treated both symptomatically and prophylactically, depending on the frequency of manifestations. Co-occurrence of hypertension, diabetes or hypercholesterolemia should be treated. Supportive care (practical help, emotional support, and counselling) is appropriate for affected individuals and their families. There are, however, recommendations for agents to avoid, such as angiography and anticoagulants which may provoke cerebrovascular accidents. It is also known that smoking increases the risk of ischemic events. Thrombolytic therapy (intravenous thrombolysis) is contraindicated because of the presumed increased risk for cerebral hemorrhage (Pagon et al., 2000; updated 2016).

Since an effective treatment for CADASIL is not available, treatments are directed towards the search of possible disease modifying strategies to mitigate clinical manifestations. However, only a few and very preliminary studies have been reported thus far.

Anecdotal cases have also used sodium valproate for such migraine treatment. Acetylcholinesterase inhibitors have been reported as not efficacious on the primary end-point in the treatment of cognitive decline (vascular dementia assessment scale after 18 weeks), but some improvement in relation to frontal-subcortical dysfunction have been observed. Antiplatelet drugs have been tested for primary and secondary stroke prevention; however, with unproven and debated benefits. Acetazolamide has been tested for an increase of cerebral perfusion evaluated by perfusion MRI, transcranial Doppler sonography and Tc-99 m extracellular domain brain perfusion SPECT. Furthermore, it has been used as prophylaxis for migraine, aiming at reducing the frequency of migraine attacks For Atorvastatin, no effects were reported on cerebral blood flow, tested with transcranial Doppler. L-arginine showed induced-vasoreactivity, tested with transcranial Doppler. Final results for Sapropterin (200-400 mg bid in 24 months) were, for the primary end-point (mean difference in reactive hyperaemia index), not significant for any improvement of peripheral vasoreactivity. In a mouse model, the combination of stem cell factor and granulocyte-colony stimulating factor were reported to restrict the pathological progression of CADASIL (all reviewed in: Di Donato et al., BMC Medicine (2017) 15:41; DOI 10.1186/s12916-017-0778-8).

In view of the evidence of a more severe disease course in individuals with vascular risk factors, particularly smoking and hypertension, control of vascular risk factors is regarded as an important part of CADASIL management. Concerning the use of antiplatelet drugs, such as aspirin or clopidogrel, most neurologists apply the guidelines used for sporadic stroke when treating CADASIL patients. However, the appropriateness of this approach is undetermined. In fact, the thrombotic genesis of ischemic events in this disease has not been proven so far. On the other hand, many reports have stressed the presence of microhaemorrhages (microbleeds) in a considerable percentage of CADASIL patients. For these reasons, the safety of antiplatelet drugs in this disease remain to be clarified. Similarly, the benefit of thrombolysis is uncertain, although it has been suggested that it is of benefit in sporadic lacunar stroke.

In a multicentre trial in 168 patients with donepezil no improvement in the primary outcome of the vascular dementia assessment scale—cognitive subscale could be observed. However, improvements were noted on several measures of executive function, but the clinical relevance of these findings is not clear. Complications of CADASIL, such as depression and migraine, appear to respond to similar treatments to those used in sporadic disease (Di Donato et al., 2017). Cerebrolysin for vascular dementia was reviewed by Chen et al. (Cochrane Database of System. Rev. 1 (2013): DOI: 10.1002/146 1858.CD008900.pub).

In the absence of specific data for CADASIL, most neurologists use aspirin in secondary prevention after ischemic strokes in older patients, for example, those aged over 40, but there is no evidence for or against its use. Whether this strategy is appropriate in CADASIL is undetermined and will require further investigation, given the possible increased haemorrhagic risk. Patients that need to undergo anticoagulation for a clear indication such as high risk atrial fibrillation should be carefully followed given the reported risk of intracerebral haemorrhage.

It is therefore evident that new, rational therapeutic interventions for CADASIL patients to address disease symptoms and disease progression are needed, especially therapeutic interventions that reduce mortality or rise survival rate, respectively.

SUMMARY

Therefore, the present invention provides Cerebrolysin for use in reducing mortality in CADASIL (cerebral autosomal dominant arteriopathy with subcortical infarcts and leukoencephalopathy) patients.

CEREBROLYSIN® (a mixture of neuropeptides derived from an enzymatic hydrolytic swine brain protein fraction and containing 15% of peptides with a molecular weight of 10,000 or less and approximately 85% of free amino acids including 3.00 mg alanine, 3.00 mg of aspartic acid, 0.06 g of cystine, 4.30 mg of glutamic acid, 1.50 mg of glycine, 1.30 mg of histidine, 2.00 mg of isoleucine, 6.00 mg of leucine, 0.50 mg of methionine, 2.00 mg of phenylalanine, 2.00 mg of proline, 0.30 g of serine. 0.30 g of threonine. 0.50 g of tryptophane and 2.00 mg of tyrosine), is a peptide preparation produced by a standardized enzymatic breakdown of brain proteins, comprising low molecular weight peptides (<10 kDa) and free amino acids.

CEREBROLYSIN® (a mixture of neuropeptides derived from an enzymatic hydrolytic swine brain protein fraction and containing 15% of peptides with a molecular weight of 10,000 or less and approximately 85% of free amino acids including 3.00 mg alanine, 3.00 mg of aspartic acid, 0.06 g of cystine, 4.30 mg of glutamic acid, 1.50 mg of glycine, 1.30 mg of histidine, 2.00 mg of isoleucine, 6.00 mg of leucine, 0.50 mg of methionine, 2.00 mg of phenylalanine, 2.00 mg of proline, 0.30 g of serine, 0.30 g of threonine, 0.50 g of tryptophane and 2.00 mg of tyrosine) is a peptide mixture with neurotrophic-like properties that amliorates behavioral and cognitive deficits in preclinical models and patients with dementia; and improves motor function, cognitive performance and activities of daily living in stroke as well as in TBI. The mode of action of cerebrolysin is pleiotrophic, ranging from neuroprotective properties such as reduced excitotoxicity and free radical formation to enhaned recovery via increased neuroplasticity and neurogenesis.

CEREBROLYSIN® (a mixture of neuropeptides derived from an enzymatic hydrolytic swine brain protein fraction and containing 15% of peptides with a molecular weight of 10,000 or less and approximately 85% of free amino acids including 3.00 mg alanine, 3.00 mg of aspartic acid, 0.06 g of cystine, 4.30 mg of glutamic acid, 1.50 mg of glycine, 1.30 mg of histidine, 2.00 mg of isoleucine, 6.00 mg of leucine, 0.50 mg of methionine, 2.00 mg of phenylalanine, 2.00 mg of proline, 0.30 g of serine, 0.30 g of threonine, 0.50 g of tryptophane and 2.00 mg of tyrosine) is used for stroke and vascular dementia. A beneficial effect on cognitive function in people with vascular dementia, possibly through decreased beta-amyloid deposition was reported. CEREBROLYSIN® (a mixture of neuropeptides derived from an enzymatic hydrolytic swine brain protein fraction and containing 15% of peptides with a molecular weight of 10,000 or less and approximately 85% of free amino acids including 3.00 mg alanine, 3.00 mg of aspartic acid, 0.06 g of cystine, 4.30 mg of glutamic acid, 1.50 mg of glycine, 1.30 mg of histidine, 2.00 mg of isoleucine, 6.00 mg of leucine, 0.50 mg of methionine, 2.00 mg of phenylalanine, 2.00 mg of proline, 0.30 g of serine, 0.30 g of threonine, 0.50 g of tryptophane and 2.00 mg of tyrosine) is approved to treat stroke in many European and Asian countries.

With the present invention, it has been surprisingly observed that CEREBROLYSIN® (a mixture of neuropeptides derived from an enzymatic hydrolytic swine brain protein fraction and containing 15% of peptides with a molecular weight of 10,000 or less and approximately 85% of free amino acids including 3.00 mg alanine, 3.00 mg of aspartic acid. 0.06 g of cystine, 4.30 mg of glutamic acid, 1.50 mg of glycine, 1.30 mg of histidine, 2.00 mg of isoleucine, 6.00 mg of leucine, 0.50 mg of methionine, 2.00 mg of phenylalanine. 2.00 mg of proline, 0.30 g of serine, 0.30 g of threonine. 0.50 g of tryptophane and 2.00 mg of tyrosine) has a significant impact on the reduction of mortality and therefore for improving survival of CADASIL patients. Although no effect was observed on white matter vacuolisation, a hallmark of CADASIL (which makes the present invention even more surprising), a highly statistically significant reduction in mortality rate was proven for CEREBROLYSIN® (a mixture of neuropeptides derived from an enzymatic hydrolytic swine brain protein fraction and containing 15% of peptides with a molecular weight of 10,000 or less and approximately 85% of free amino acids including 3.00 mg alanine. 3.00 mg of aspartic acid, 0.06 g of cystine, 4.30 mg of glutamic acid, 1.50 mg of glycine, 1.30 mg of histidine, 2.00 mg of isoleucine, 6.00 mg of leucine. 0.50 mg of methionine, 2.00 mg of phenylalanine. 2.00 mg of proline, 0.30 g of serine, 0.30 g of threonine, 0.50 g of tryptophane and 2.00 mg of tyrosine) treatment in a state of the art CADASIL mouse model.

This effect was completely unexpected, specifically in view of the fact that in a prior publication it was reported that there is no in vitro protective effect of CEREBROLYSIN® (a mixture of neuropeptides derived from an enzymatic hydrolytic swine brain protein fraction and containing 15% of peptides with a molecular weight of 10,000 or less and approximately 85% of free amino acids including 3.00 mg alanine, 3.00 mg of aspartic acid, 0.06 g of cystine, 4.30 mg of glutamic acid, 1.50 mg of glycine. 1.30 mg of histidine, 2.00 mg of isoleucine. 6.00 mg of leucine, 0.50 mg of methionine, 2.00 mg of phenylalanine, 2.00 mg of proline, 0.30 g of serine, 0.30 g of threonine, 0.50 g of tryptophane and 2.00 mg of tyrosine) against oxidative stress-induced apoptosis in cells from CADASIL patients (Formichi et al., Neurol. Sci. 34 (2013), 553-556; doi: 10.1007/s10072-012-1174-y).

In this study. Formichi et al. used peripheral blood lymphocytes (PBLs) from 15 CADASIL patients (age range 34-70 years) and 2-deoxy-D-ribose (dRib), a highly reducing sugar, as paradigm pro-apoptotic stimulus. Apoptosis was analysed by flow cytometry and fluorescence microscopy. Administration of CEREBROLYSIN® (a mixture of neuropeptides derived from an enzymatic hydrolytic swine brain protein fraction and containing 15% of peptides with a molecular weight of 10,000 or less and approximately 85% of free amino acids including 3.00 mg alanine. 3.00 mg of aspartic acid, 0.06 g of cystine, 4.30 mg of glutamic acid, 1.50 mg of glycine, 1.30 mg of histidine, 2.00 mg of isoleucine. 6.00 mg of leucine, 0.50 mg of methionine, 2.00 mg of phenylalanine. 2.00 mg of proline. 0.30 g of serine. 0.30 g of threonine. 0.50 g of tryptophane and 2.00 mg of tyrosine) to PBLs from CADASIL patients cultured under standard conditions had no effect on the percentage of apoptotic cells. Administration of Cere to PBLs cultured with dRib caused a significant decrease in apoptosis after 48 h of culture in only 5 patients, whereas in the other 10 patients, CEREBROLYSIN® (a mixture of neuropeptides derived from an enzymatic hydrolytic swine brain protein fraction and containing 15% of peptides with a molecular weight of 10,000 or less and approximately 85% of free amino acids including 3.00 mg alanine, 3.00 mg of aspartic acid, 0.06 g of cystine, 4.30 mg of glutamic acid, 1.50 mg of glycine. 1.30 mg of histidine, 2.00 mg of isoleucine, 6.00 mg of leucine, 0.50 mg of methionine. 2.00 mg of phenylalanine. 2.00 mg of proline. 0.30 g of serine, 0.30 g of threonine, 0.50 g of tryptophane and 2.00 mg of tyrosine) treatment was not associated with any significant difference in the percentage of apoptosis. This result showed a protective effect of CEREBROLYSIN® (a mixture of neuropeptides derived from an enzymatic hydrolytic swine brain protein fraction and containing 15% of peptides with a molecular weight of 10,000 or less and approximately 85% of free amino acids including 3.00 mg alanine. 3.00 mg of aspartic acid. 0.06 g of cystine. 4.30 mg of glutamic acid, 1.50 mg of glycine, 1.30 mg of histidine, 2.00 mg of isoleucine. 6.00 mg of leucine, 0.50 mg of methionine, 2.00 mg of phenylalanine, 2.00 mg of proline. 0.30 g of serine. 0.30 g of threonine, 0.50 g of tryptophane and 2.00 mg of tyrosine) against oxidative stress-induced apoptosis only in 30% of the CADASIL patients. It was therefore concluded that the Notch3 gene probably does not influence the anti-apoptotic properties of CEREBROLYSIN® (a mixture of neuropeptides derived from an enzymatic hydrolytic swine brain protein fraction and containing 15% of peptides with a molecular weight of 10,000 or less and approximately 85% of free amino acids including 3.00 mg alanine, 3.00 mg of aspartic acid, 0.06 g of cystine, 4.30 mg of glutamic acid, 1.50 mg of glycine. 1.30 mg of histidine, 2.00 mg of isoleucine, 6.00 mg of leucine. 0.50 mg of methionine. 2.00 mg of phenylalanine. 2.00 mg of proline, 0.30 g of serine, 0.30 g of threonine, 0.50 g of tryptophane and 2.00 mg of tyrosine) in vitro. This could also explain the result obtained in the course of the present invention that CEREBROLYSIN® (a mixture of neuropeptides derived from an enzymatic hydrolytic swine brain protein fraction and containing 15% of peptides with a molecular weight of 10.000 or less and approximately 85% of free amino acids including 3.00 mg alanine, 3.00 mg of aspartic acid, 0.06 g of cystine, 4.30 mg of glutamic acid, 1.50 mg of glycine, 1.30 mg of histidine, 2.00 mg of isoleucine, 6.00 mg of leucine, 0.50 mg of methionine. 2.00 mg of phenylalanine, 2.00 mg of proline, 0.30 g of serine, 0.30 g of threonine, 0.50 g of tryptophane and 2.00 mg of tyrosine) has no effect on vacuolisation. In any way, it was therefore completely unexpected that CEREBROLYSIN® (a mixture of neuropeptides derived from an enzymatic hydrolytic swine brain protein fraction and containing 15% of peptides with a molecular weight of 10.000 or less and approximately 85% of free amino acids including 3.00 mg alanine. 3.00 mg of aspartic acid, 0.06 g of cystine, 4.30 mg of glutamic acid, 1.50 mg of glycine, 1.30 mg of histidine, 2.00 mg of isoleucine, 6.00 mg of leucine, 0.50 mg of methionine, 2.00 mg of phenylalanine. 2.00 mg of proline, 0.30 g of serine, 0.30 g of threonine, 0.50 g of tryptophane and 2.00 mg of tyrosine) could have an effect on the primary parameter mortality.

Despite the results obtained by Formichi et al., and despite the fact that CADASIL patients have a mutation of Notch3 gene, CEREBROLYSIN® (a mixture of neuropeptides derived from an enzymatic hydrolytic swine brain protein fraction and containing 15% of peptides with a molecular weight of 10,000 or less and approximately 85% of free amino acids including 3.00 mg alanine, 3.00 mg of aspartic acid, 0.06 g of cystine, 4.30 mg of glutamic acid, 1.50 mg of glycine, 1.30 mg of histidine, 2.00 mg of isoleucine, 6.00 mg of leucine, 0.50 mg of methionine, 2.00 mg of phenylalanine, 2.00 mg of proline, 0.30 g of serine, 0.30 g of threonine, 0.50 g of tryptophane and 2.00 mg of tyrosine) can be effectively applied to treat all CADASIL patients so as to obtain the effects according to the present invention.

CADASIL is usually diagnosed genetically, preferably by sequencing the whole Notch3 gene. Heterozygous truncating pathogenic variants in NOTCH3 exon 33 (encoding the PEST domains of the intracellular part of the protein) have been described in lateral meningeal syndrome (Lehman syndrome). These pathogenic variants are presumed to act via a gain of Notch3 signalling function, and are distinct from NOTCH3 pathogenic variants in CADASIL. A Notch3 exon 25 pathogenic variant (c.4556T>C. p.Leu1519Pro) has been described in autosomal dominant infantile myofibromatosis.

Cerebral magnetic resonance images (MRIs) of CADASIL patients show hypointensities on T1-weighted images and hyperintensities on T2-weighted images, usually multiple confluent white matter lesions of various sizes, are characteristic. These lesions are concentrated around the basal ganglia, peri-ventricular white matter, and the pons, and are similar to those seen in Binswanger disease. These white matter lesions are also seen in asymptomatic individuals with the mutated gene. While MRI is not used to diagnose CADASIL, it can show the progression of white matter changes even decades before onset of symptoms.

White matter changes in CADASIL patients often involve the anterior temporal lobe, the external capsule and the superior frontal gyrus. Anterior temporal pole changes have been shown to have a high sensitivity and specificity for the disease (approximatively 90% for each) and are useful in diagnosis. In Asian populations, anterior temporal lobe involvement is less common. External capsule changes also have a high sensitivity (approximatively 90%) but a lower specificity (approximately 50%). In fact, a recent systematic analysis showed a similar involvement of the external capsule in CADASIL and sporadic SVD. Corpus callosal signal abnormalities, rarely occurring in sporadic SVD, are described in CADASIL; such abnormalities are also a feature of multiple sclerosis, which is one reason for the misdiagnosis of CADASIL as multiple sclerosis. Cerebral microbleeds, which are shown by Gradient-echo images with dot-like hypointense lesions, occur in a variable proportion of cases (30-70%) and usually increase with age and risk factors such as high blood pressure, and intracerebral haemorrhage have also been described in a number of patients, especially those of Asian origin (di Donato et al., 2017).

CADASIL is ICD-10-CM Diagnosis Code classified as 167.8 ("Other specified cerebrovascular diseases") and has been defined as a subcortical disease, but recent studies with high-field 7-Tesla MRI, which allows higher resolution imaging, have detected primary involvement of the cortex, including the demonstration of cortical microinfarcts and early diffuse cortical alterations in frontal and parietal regions most often following a symmetrical pattern in both hemispheres. These changes were not related to cortical thinning or to subcortical lesions and have been hypothesized to be secondary to venous vascular density or intramyelin oedema. Similar data have also been reported in experimental models. Moreover, subcortical changes might induce secondary cortical changes. In a longitudinal study, incident lacunes were followed by cortical thinning specifically in connected brain regions. Another recent development is the use of diffusion tensor imaging to characterize tissue damage. The typical change in diffusion metrics observed in CADASIL patients is a reduction in fractional anisotropy (a measure for the directionality of diffusion) and an increase in the apparent diffusion coefficient or mean diffusivity (a measure for the extent of diffusion). Histogram analysis has been proposed as a sensitive tool to measure CADASIL-related changes cross-sectionally as well as longitudinally (diagnosis and differential diagnosis reviewed in di Donato et al., 2017 and Rutten et al., 2000, updated 2016).

Although still regarded as being underdiagnosed. CADASIL diagnosis has significantly improved in the last 20 years and is now much more accurate.

CEREBROLYSIN® (a mixture of neuropeptides derived from an enzymatic hydrolytic swine brain protein fraction and containing 15% of peptides with a molecular weight of 10,000 or less and approximately 85% of free amino acids including 3.00 mg alanine. 3.00 mg of aspartic acid. 0.06 g of cystine, 4.30 mg of glutamic acid, 1.50 mg of glycine. 1.30 mg of histidine. 2.00 mg of isoleucine. 6.00 mg of leucine, 0.50 mg of methionine, 2.00 mg of phenylalanine, 2.00 mg of proline. 0.30 g of serine. 0.30 g of threonine, 0.50 g of tryptophane and 2.00 mg of tyrosine) is a pharmaceutical preparation of proteolytically generated neuropeptides derived from purified brain proteins. CEREBROLYSIN® (a mixture of neuropeptides derived from an enzymatic hydrolytic swine brain protein fraction and containing 15% of peptides with a molecular weight of 10,000 or less and approximately 85% of free amino acids including 3.00 mg alanine. 3.00 mg of aspartic acid. 0.06 g of cystine, 4.30 mg of glutamic acid, 1.50 mg of glycine, 1.30 mg of histidine. 2.00 mg of isoleucine, 6.00 mg of leucine. 0.50 mg of methionine, 2.00 mg of phenylalanine, 2.00 mg of proline. 0.30 g of serine, 0.30 g of threonine. 0.50 g of tryptophane and 2.00 mg of tyrosine) is available on the market, often as standardised product. CEREBROLYSIN® (a mixture of neuropeptides derived from an enzymatic hydrolytic swine brain protein fraction and containing 15% of peptides with a molecular weight of 10,000 or less and approximately 85% of free amino acids including 3.00 mg alanine, 3.00 mg of aspartic acid, 0.06 g of cystine, 4.30 mg of glutamic acid, 1.50 mg of glycine, 1.30 mg of histidine, 2.00 mg of isoleucine, 6.00 mg of leucine, 0.50 mg of methionine. 2.00 mg of phenylalanine, 2.00 mg of proline, 0.30 g of serine, 0.30 g of threonine, 0.50 g of tryptophane and 2.00 mg of tyrosine) comprises 15 to 30% low molecular weight peptides (<10 kDa) and 70 to 85% free amino acids such as alanine, aspartic acid, arginine, glutamic acid, glycine, histidine, isoleucine, leucine, lysine, methionine, phenylalanine, proline, serine, threonine, tryptophan, cysteine and valine. The solution is preferably sterile and ready for injection or infusion (i.e. it fulfils all standards and requirements for pharmaceutical preparations to be administered to human patients). CEREBROLYSIN® (a mixture of neuropeptides derived from an enzymatic hydrolytic swine brain protein fraction and containing 15% of peptides with a molecular weight of 10,000 or less and approximately 85% of free amino acids including 3.00 mg alanine. 3.00 mg of aspartic acid. 0.06 g of cystine, 4.30 mg of glutamic acid, 1.50 mg of glycine, 1.30 mg of histidine, 2.00 mg of isoleucine, 6.00 mg of leucine. 0.50 mg of methionine, 2.00 mg of phenylalanine, 2.00 mg of proline. 0.30 g of serine, 0.30 g of threonine, 0.50 g of tryptophane and 2.00 mg of tyrosine) preparations are disclosed in EP 0 452 299 A1 CN and Gromova et al. (Difficult Patient 8 (2010), 25-31).

Preferred CEREBROLYSIN® (a mixture of neuropeptides derived from an enzymatic hydrolytic swine brain protein fraction and containing 15% of peptides with a molecular weight of 10,000 or less and approximately 85% of free amino acids including 3.00 mg alanine. 3.00 mg of aspartic acid, 0.06 g of cystine, 4.30 mg of glutamic acid, 1.50 mg of glycine, 1.30 mg of histidine, 2.00 mg of isoleucine. 6.00 mg of leucine, 0.50 mg of methionine, 2.00 mg of phenylalanine, 2.00 mg of proline, 0.30 g of serine, 0.30 g of threonine, 0.50 g of tryptophane and 2.00 mg of tyrosine) concentrations to be used according to the present invention contain 50 to 1000 mg, preferably 100 to 500 mg, especially 150 to 250 mg, of CEREBROLYSIN® concentrate (a mixture of neuropeptides derived from an enzymatic hydrolytic swine brain protein fraction and containing 15% of peptides with a molecular weight of 10,000 or less and approximately 85% of free amino acids including 3.00 mg alanine. 3.00 mg of aspartic acid. 0.06 g of cystine, 4.30 mg of glutamic acid, 1.50 mg of glycine. 1.30 mg of histidine. 2.00 mg of isoleucine, 6.00 mg of leucine, 0.50 mg of methionine, 2.00 mg of phenylalanine, 2.00 mg of proline. 0.30 g of serine, 0.30 g of threonine, 0.50 g of tryptophane and 2.00 mg of tyrosine) per ml in aqueous solution. As already stated above, CEREBROLYSIN® (a mixture of neuropeptides derived from an enzymatic hydrolytic swine brain protein fraction and containing 15% of peptides with a molecular weight of 10,000 or less and approximately 85% of free amino acids including 3.00 mg alanine. 3.00 mg of aspartic acid, 0.06 g of cystine, 4.30 mg of glutamic acid. 1.50 mg of glycine. 1.30 mg of histidine, 2.00 mg of isoleucine, 6.00 mg of leucine, 0.50 mg of methionine. 2.00 mg of phenylalanine. 2.00 mg of proline, 0.30 g of serine. 0.30 g of threonine. 0.50 g of tryptophane and 2.00 mg of tyrosine) contains approximately 85% free amino acids and 15% low molecular weight peptides (<10 kDa), based on the total nitrogen content.

CEREBROLYSIN® concentrate has a standardised content of specific amino acids, i.e., a mixture of neuropeptides derived from an enzymatic hydrolytic swine brain protein fraction and containing 15% of peptides with a molecular weight of 10.000 or less and approximately 85% of free amino acids including 3.00 mg alanine. 3.00 mg of aspartic acid, 0.06 g of cystine, 4.30 mg of glutamic acid, 1.50 mg of glycine, 1.30 mg of histidine, 2.00 mg of isoleucine, 6.00 mg of leucine, 0.50 mg of methionine. 2.00 mg of phenylalanine. 2.00 mg of proline, 0.30 g of serine, 0.30 g of threonine, 0.50 g of tryptophane and 2.00 mg of tyrosine. In the concentrate (the concentration of which may be varied, if necessary, at administration), CEREBROLYSIN® has the following amino acid content (in mg/ml of CEREBROLYSIN® concentrate): alanine: 2.40 to 3.60, especially 3.10 to 3.50; aspartic acid: 2.40 to 3.60, especially 2.20 to 3.50; valine: 1.60 to 2.40, especially 2.10 to 2.40; histidine:

1.04-1.56, especially 1.10 to 1.50; glycine: 1.20 to 1.80, especially 1.60 to 1.90; glutamic acid: 3.20-4.80, especially 3.30 to 4.60; isoleucine: 1.60 to 2.40, especially 2.20 to 2.40; leucine: 4.80 to 7.20, especially 5.70 to 6.30; lysine: 4.80 to 7.20, especially 5.80 to 7.20; methionine: 0.35 to 0.65, especially 0.40 to 0.70; proline: 1.60 to 2.40, especially 2.00 to 2.40; serine: 0.21 to 0.39, especially 0.23 to 0.36; threonine: 0.21 to 0.39, especially 0.26 to 0.35; tryptophane: 0.35 to 0.65, especially 0.40 to 0.70; phenylalanine: 1.60 to 2.40, especially 1.60 to 2.40, i.e., a mixture of neuropeptides derived from an enzymatic hydrolytic swine brain protein fraction and containing 15% of peptides with a molecular weight of 10,000 or less and approximately 85% of free amino acids including 3.00 mg alanine, 3.00 mg of aspartic acid, 0.06 g of cystine, 4.30 mg of glutamic acid, 1.50 mg of glycine, 1.30 mg of histidine, 2.00 mg of isoleucine. 6.00 mg of leucine, 0.50 mg of methionine. 2.00 mg of phenylalanine, 2.00 mg of proline, 0.30 g of serine, 0.30 g of threonine, 0.50 g of tryptophane and 2.00 mg of tyrosine. It is clear that upon dilution of this concentrate, the absolute amount of a specific amino acid per ml decreases; however, the relative ratio of the amino acid with respect to each other and with respect to the low molecular weight peptides (of 10.000 or less), said relative ratio being an essential element for the therapeutic effects obtained with the present invention) remains the same upon dilution.

A method for producing CEREBROLYSIN® (a mixture of neuropeptides derived from an enzymatic hydrolytic swine brain protein fraction and containing 15% of peptides with a molecular weight of 10.000 or less and approximately 85% of free amino acids including 3.00 mg alanine, 3.00 mg of aspartic acid, 0.06 g of cystine, 4.30 mg of glutamic acid, 1.50 mg of glycine. 1.30 mg of histidine, 2.00 mg of isoleucine, 6.00 mg of leucine, 0.50 mg of methionine, 2.00 mg of phenylalanine, 2.00 mg of proline, 0.30 g of serine. 0.30 g of threonine, 0.50 g of tryptophane and 2.00 mg of tyrosine) is disclosed in EP 0 452 299 A1 and is obtained from enzymatic hydrolysis of swine brain protein fraction. Each ml of this product contains 3.00 mg of alanine. 3.00 mg of aspartic acid. 0.06 g of cystine, 4.30 mg of glutamic acid, 1.50 mg of glycine, 1.30 mg of histidine, 2.00 mg of isoleucine, 6.00 mg of leucine. 0.50 mg of methionine, 2.00 mg of phenylalanine, 2.00 mg of proline. 0.30 g of serine. 0.30 g of threonine, 0.50 g of tryptophane and 2.00 mg of thyrosine as amino acids as well as peptides having a molecular weight of 10.000 or less. The mixture of peptides and amino acids in the preparations disclosed in EP 0 452 299 A1 contained (as for a typical CEREBROLYSIN® product (a mixture of neuropeptides derived from an enzymatic hydrolytic swine brain protein fraction and containing 15% of peptides with a molecular weight of 10,000 or less and approximately 85% of free amino acids including 3.00 mg alanine. 3.00 mg of aspartic acid. 0.06 g of cystine, 4.30 mg of glutamic acid, 1.50 mg of glycine, 1.30 mg of histidine, 2.00 mg of isoleucine, 6.00 mg of leucine. 0.50 mg of methionine, 2.00 mg of phenylalanine. 2.00 mg of proline. 0.30 g of serine. 0.30 g of threonine, 0.50 g of tryptophane and 2.00 mg of tyrosine)) approximately 15% of peptides with a molecular weight of 10,000 or less and approximately 85% of free amino acid.

The dose applied may preferably be in the range of 100 to 10 000 mg (0.5 to 50 ml CEREBROLYSIN® concentrate (a mixture of neuropeptides derived from an enzymatic hydrolytic swine brain protein fraction and containing 15% of peptides with a molecular weight of 10,000 or less and approximately 85% of free amino acids including 3.00 mg alanine. 3.00 mg of aspartic acid, 0.06 g of cystine, 4.30 mg of glutamic acid, 1.50 mg of glycine, 1.30 mg of histidine, 2.00 mg of isoleucine, 6.00 mg of leucine, 0.50 mg of methionine, 2.00 mg of phenylalanine. 2.00 mg of proline. 0.30 g of serine, 0.30 g of threonine, 0.50 g of tryptophane and 2.00 mg of tyrosine)). Preferably, the CADASIL patient is treated with a dose in the range of 0.1 to 100 ml, preferably 1 to 50 ml, of cerebrolysin, corresponding to 21.5 to 21,520 mg of CEREBROLYSIN® concentrate (a mixture of neuropeptides derived from an enzymatic hydrolytic swine brain protein fraction and containing 15% of peptides with a molecular weight of 10.000 or less and approximately 85% of free amino acids including 3.00 mg alanine, 3.00 mg of aspartic acid, 0.06 g of cystine, 4.30 mg of glutamic acid, 1.50 mg of glycine. 1.30 mg of histidine, 2.00 mg of isoleucine. 6.00 mg of leucine, 0.50 mg of methionine. 2.00 mg of phenylalanine. 2.00 mg of proline, 0.30 g of serine, 0.30 g of threonine, 0.50 g of tryptophane and 2.00 mg of tyrosine) (a preferred CEREBROLYSIN® concentrate (a mixture of neuropeptides derived from an enzymatic hydrolytic swine brain protein fraction and containing 15% of peptides with a molecular weight of 10,000 or less and approximately 85% of free amino acids including 3.00 mg alanine, 3.00 mg of aspartic acid, 0.06 g of cystine, 4.30 mg of glutamic acid, 1.50 mg of glycine, 1.30 mg of histidine. 2.00 mg of isoleucine, 6.00 mg of leucine, 0.50 mg of methionine, 2.00 mg of phenylalanine, 2.00 mg of proline, 0.30 g of serine, 0.30 g of threonine, 0.50 g of tryptophane and 2.00 mg of tyrosine) contains 215.2 mg/ml). If applied intramuscularly, the dose is usually lower than intravenously (e.g., preferably 0.5 to 5 ml and preferably 0.5 to 10 ml, intravenously). Preferably, the CADASIL patient is therefore treated with an intramuscularly administered dose of 0.1 to 10 ml, preferably 0.5 to 5 ml, corresponding to 21.5 mg to 2152 mg CEREBROLYSIN® concentrate (a mixture of neuropeptides derived from an enzymatic hydrolytic swine brain protein fraction and containing 15% of peptides with a molecular weight of 10,000 or less and approximately 85% of free amino acids including 3.00 mg alanine. 3.00 mg of aspartic acid, 0.06 g of cystine. 4.30 mg of glutamic acid, 1.50 mg of glycine, 1.30 mg of histidine, 2.00 mg of isoleucine, 6.00 mg of leucine, 0.50 mg of methionine, 2.00 mg of phenylalanine, 2.00 mg of proline. 0.30 g of serine. 0.30 g of threonine. 0.50 g of tryptophane and 2.00 mg of tyrosine). CEREBROLYSIN® (a mixture of neuropeptides derived from an enzymatic hydrolytic swine brain protein fraction and containing 15% of peptides with a molecular weight of 10,000 or less and approximately 85% of free amino acids including 3.00 mg alanine, 3.00 mg of aspartic acid, 0.06 g of cystine. 4.30 mg of glutamic acid, 1.50 mg of glycine, 1.30 mg of histidine, 2.00 mg of isoleucine, 6.00 mg of leucine. 0.50 mg of methionine, 2.00 mg of phenylalanine. 2.00 mg of proline, 0.30 g of serine, 0.30 g of threonine. 0.50 g of tryptophane and 2.00 mg of tyrosine) may also be continuously infused (usually at volumes above 10 ml) and the CEREBROLYSIN® concentrate (a mixture of neuropeptides derived from an enzymatic hydrolytic swine brain protein fraction and containing 15% of peptides with a molecular weight of 10,000 or less and approximately 85% of free amino acids including 3.00 mg alanine. 3.00 mg of aspartic acid. 0.06 g of cystine, 4.30 mg of glutamic acid, 1.50 mg of glycine. 1.30 mg of histidine, 2.00 mg of isoleucine, 6.00 mg of leucine, 0.50 mg of methionine, 2.00 mg of phenylalanine. 2.00 mg of proline, 0.30 g of serine, 0.30 g of threonine, 0.50 g of tryptophane and 2.00 mg of tyrosine) may therefore e.g. be diluted with 0.9% sodium chloride solution (9 mg NaCl/ml), Ringer's solution (Na+ 153.98 mmol/l, Ca2+2.74 mmol/l, K+4.02 mmol/l.

Cl-163.48 mmol/l), 5% glucose. Infusion durations of typically 5 min to 4 h, preferably 10 min to 2 h, especially 15 to 60 min may be performed (preferably each day) e.g. for 1 to 100 d, preferably from 5 to 50 d, preferably from 10 to 30 d (usually, the administration is performed only on working days, not on weekends, so that usually a treatment cycle is applied in 3-5×5 consecutive days of administration). According to a preferred embodiment, the CADASIL patient is treated with an intravenously administered dose of 0.1 to 100 ml, preferably 1 to 50 ml, corresponding to 215.2 to 21,520 mg CEREBROLYSIN® concentrate (a mixture of neuropeptides derived from an enzymatic hydrolytic swine brain protein fraction and containing 15% of peptides with a molecular weight of 10,000 or less and approximately 85% of free amino acids including 3.00 mg alanine, 3.00 mg of aspartic acid. 0.06 g of cystine, 4.30 mg of glutamic acid, 1.50 mg of glycine, 1.30 mg of histidine, 2.00 mg of isoleucine. 6.00 mg of leucine, 0.50 mg of methionine, 2.00 mg of phenylalanine, 2.00 mg of proline, 0.30 g of serine. 0.30 g of threonine. 0.50 g of tryptophane and 2.00 mg of tyrosine).

Treatment cycles can be repeated after a treatment-free period from 1 to 6, from 1 to 3, preferably 2 to 3, months.

The present invention is further illustrated by the following examples and the figures, yet without being limited thereto.

FIG. 1 shows the calculated mortality rate of the saline treated mice cohort versus the cerebrolysin group (35% vs. 0%).

Figure 2:
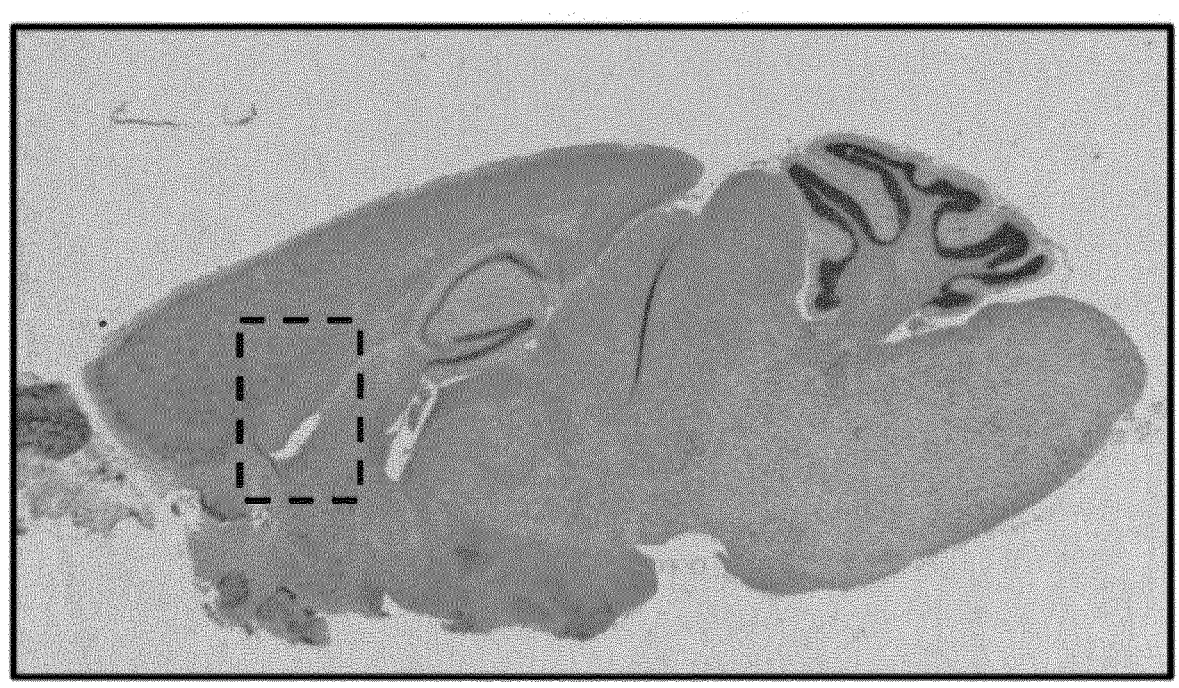

FIG. 2 shows luxol fast blue and Nissl stained sagittal brain cut of a CADASIL mouse 0.5 mm laterally of the middle line. Cell body is dark blue: white matter imposes turquoise. The dashed line comprises the region observed, anterior corpus callosum.

FIG. 3 shows anterior corpus callosum in a young, healthy mouse (A) and in an 18 months old CADASIL mouse (B). No vacuolisation occurs in the anterior medial corpus callosum of six weeks old male C57BL/6 (A), and pronounced vacuolization in CADASIL mice (B). In contrast to round vacuoles, vessels are visible as elongated structures (see inner frame)).

Figure 4:
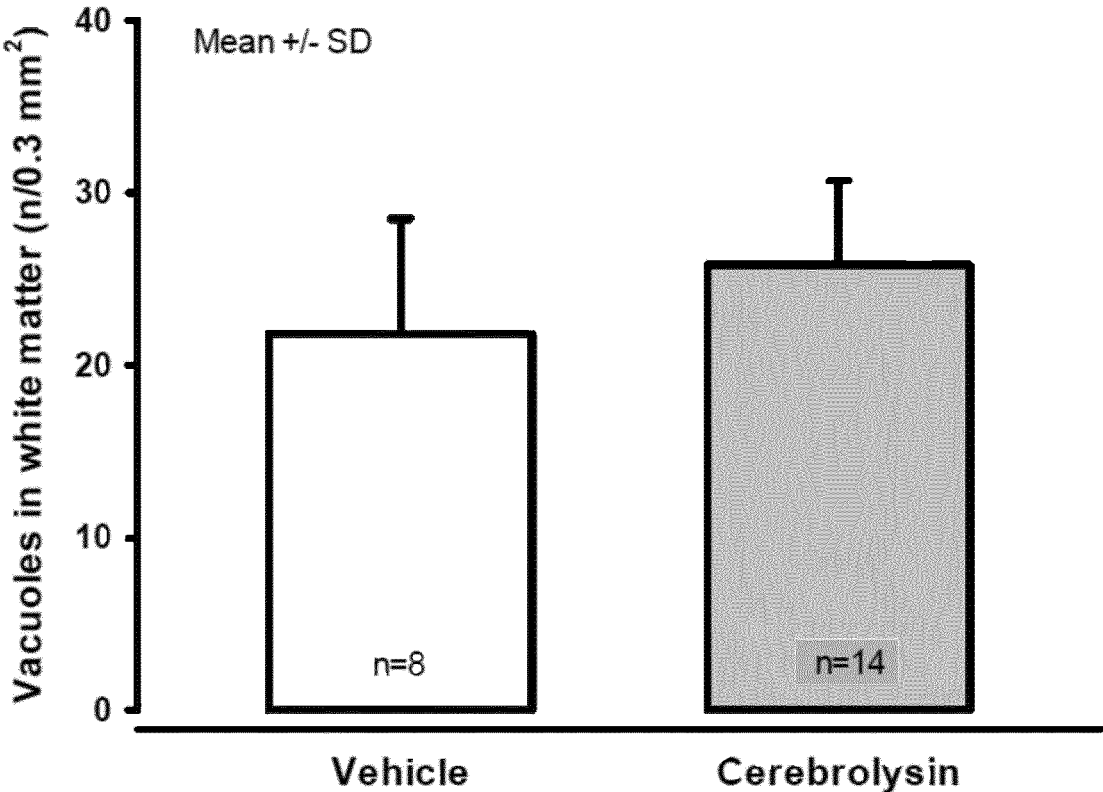

FIG. 4 shows the number of vacuoles in anteriore corpus callosum of 18 months old CADASIL transgenic mice treated between month 12 to 18 with three cycles of vehicle (left) or cerebrolysin (right). In both groups, the expected pathology was observed. i.e. the vacuolation of white matter (no statistically significant difference between both groups (p=0.12: Student t-test)).

EXAMPLES

Therapeutic effect of CEREBROLYSIN® (a mixture of neuropeptides derived from an enzymatic hydrolytic swine brain protein fraction and containing 15% of peptides with a molecular weight of 10,000 or less and approximately 85% of free amino acids including 3.00 mg alanine, 3.00 mg of aspartic acid, 0.06 g of cystine, 4.30 mg of glutamic acid, 1.50 mg of glycine, 1.30 mg of histidine, 2.00 mg of isoleucine, 6.00 mg of leucine, 0.50 mg of methionine, 2.00 mg of phenylalanine, 2.00 mg of proline, 0.30 g of serine, 0.30 g of threonine, 0.50 g of tryptophane and 2.00 mg of tyrosine) in a murine model of CADASIL
Materials and Methods
CADASIL Mouse Model: NOTCH3R169C Mutation (Line 88)

The proof of concept study to examine the therapeutic effect of CEREBROLYSIN® (a mixture of neuropeptides derived from an enzymatic hydrolytic swine brain protein fraction and containing 15% of peptides with a molecular weight of 10.000 or less and approximately 85% of free amino acids including 3.00 mg alanine. 3.00 mg of aspartic acid, 0.06 g of cystine, 4.30 mg of glutamic acid, 1.50 mg of glycine. 1.30 mg of histidine, 2.00 mg of isoleucine, 6.00 mg of leucine. 0.50 mg of methionine, 2.00 mg of phenylalanine, 2.00 mg of proline. 0.30 g of serine. 0.30 g of threonine. 0.50 g of tryptophane and 2.00 mg of tyrosine) in CADASIL was carried out in an established transgenic CADASIL mouse model, expressing the NOTCH3R 169C mutation (line 88). This specific arginine to cysteine substitution at residue 169 in exon 4 has been described in CADASIL patients and appears to be a frequent mutation (Joutel et al., 1997). This transgenic mouse strain has previously been characterised in detail to display several of the biochemical aspects of CADASIL and is thus considered a suitable genetic animal model for the disease (Ghosh et al., 2015; Joutel et al., 2010). Joutel and colleagues (Joutel et al., 2010) demonstrated that the in vivo expression of the mutated transgene in the mouse reproduced the endogenous NOTCH3 expression pattern and main pathological features of CADASIL, including typical NOTCH3ECD aggregates, GOM deposits in brain vessels, progressive white matter damage and reduced cerebral blood flow. Mutant mice displayed attenuated myogenic responses and reduced calibre of brain arteries, as well as impaired cerebrovascular autoregulation, functional hyperemia and a substantial reduction of white matter capillary density. A recent characterisation of the NOTCH3R 169C model revealed the important role of pericytes in the dysfunction of cerebral vessels and BBB leakage, which is causal to CADASIL pathology (Ghosh et al., 2015). The authors showed that with increasing age, mutated NOTCH3 aggregated around pericytes and smooth muscle cells. NOTCH3 accumulation caused apoptosis leading to significant reduction of pericyte number and coverage of capillaries by pericyte processes. These changes were associated with detachment of astrocytic end-feet from cerebral microvessels, opening of the BBB and microvascular dysfunction, as measured by leakage of plasma proteins, reduction in expression of endothelial adherens junction proteins and reduced microvascular reactivity to carbon dioxide.
Experimental Conduct:

To assess the effect of CEREBROLYSIN® (a mixture of neuropeptides derived from an enzymatic hydrolytic swine brain protein fraction and containing 15% of peptides with a molecular weight of 10,000 or less and approximately 85% of free amino acids including 3.00 mg alanine, 3.00 mg of aspartic acid, 0.06 g of cystine, 4.30 mg of glutamic acid. 1.50 mg of glycine, 1.30 mg of histidine, 2.00 mg of isoleucine. 6.00 mg of leucine, 0.50 mg of methionine, 2.00 mg of phenylalanine. 2.00 mg of proline, 0.30 g of serine, 0.30 g of threonine, 0.50 g of tryptophane and 2.00 mg of tyrosine) in this CADASIL mouse model 28 animals were bred and allowed to age over 12 months, before initiation of three treatment cycles. Mutant mice were administered 2.5 ml/kg CEREBROLYSIN® (a mixture of neuropeptides derived from an enzymatic hydrolytic swine brain protein fraction and containing 15% of peptides with a molecular weight of 10,000 or less and approximately 85% of free amino acids including 3.00 mg alanine, 3.00 mg of aspartic acid, 0.06 g of cystine, 4.30 mg of glutamic acid, 1.50 mg of glycine, 1.30 mg of histidine, 2.00 mg of isoleucine, 6.00 mg of leucine. 0.50 mg of methionine, 2.00 mg of phenylalanine, 2.00 mg of proline, 0.30 g of serine, 0.30 g of threonine, 0.50 g of tryptophane and 2.00 mg of tyrosine)

diluted in 0.9% saline or saline alone. Treatment was applied in a randomized and completely blinded manner in 3-week cycles of 5 weekly IP injections (3×15 injections per mouse per treatment in total). Animals were treated at an age of 12, 14 and 16 months, respectively, and sacrificed for analysis at 18 months of age. This treatment regime was chosen based on data obtained in experimental studies testing the therapeutic CEREBROLYSIN® (a mixture of neuropeptides derived from an enzymatic hydrolytic swine brain protein fraction and containing 15% of peptides with a molecular weight of 10,000 or less and approximately 85% of free amino acids including 3.00 mg alanine, 3.00 mg of aspartic acid, 0.06 g of cystine, 4.30 mg of glutamic acid, 1.50 mg of glycine, 1.30 mg of histidine, 2.00 mg of isoleucine, 6.00 mg of leucine, 0.50 mg of methionine, 2.00 mg of phenyl-alanine, 2.00 mg of proline, 0.30 g of serine, 0.30 g of threonine, 0.50 g of tryptophane and 2.00 mg of tyrosine) effect in different neurodegenerative disorders. The rationale for a 12-month aging process prior to treatment initiation stemmed from the observation that mice of this model start to display typical disease features of CADASIL at around this age (Joutel et al., 2010).

Further, considering the translational aspect a therapeutic rather than preventive intervention approach was selected to represent a realistic clinical situation, where therapy would start once the pathology has advanced to a stage to allow diagnosis. Mortality was chosen as primary parameter, representing a robust and clinically valid outcome measure. In addition, the extend of CADASIL-specific white matter lesions was quantified by histology analysis using luxol fast blue staining. To this end, animals were perfused and brains were embedded in paraffin. Per animal two counting areas in three sagittal cuts in the anterior medial corpus callosum were examined.

Results

CEREBROLYSIN® (a mixture of neuropeptides derived from an enzymatic hydrolytic swine brain protein fraction and containing 15% of peptides with a molecular weight of 10,000 or less and approximately 85% of free amino acids including 3.00 mg alanine, 3.00 mg of aspartic acid, 0.06 g of cystine, 4.30 mg of glutamic acid, 1.50 mg of glycine, 1.30 mg of histidine, 2.00 mg of isoleucine, 6.00 mg of leucine, 0.50 mg of methionine, 2.00 mg of phenylalanine, 2.00 mg of proline, 0.30 g of serine, 0.30 g of threonine, 0.50 g of tryptophane and 2.00 mg of tyrosine) treatment completely prevented mortality of CADASIL transgenic mice. Over the observation period of 12 to 18 months (corresponding to animal age) 5 out of 14 mice in the control group died (36%), however, not a single animal of the CEREBROLYSIN® (a mixture of neuropeptides derived from an enzymatic hydrolytic swine brain protein fraction and containing 15% of peptides with a molecular weight of 10,000 or less and approximately 85% of free amino acids including 3.00 mg alanine, 3.00 mg of aspartic acid, 0.06 g of cystine, 4.30 mg of glutamic acid, 1.50 mg of glycine, 1.30 mg of histidine, 2.00 mg of isoleucine, 6.00 mg of leucine, 0.50 mg of methionine, 2.00 mg of phenylalanine, 2.00 mg of proline, 0.30 g of serine, 0.30 g of threonine, 0.50 g of tryptophane and 2.00 mg of tyrosine)-treated deceased. The calculated mortality rate of saline treated cohort was 35% versus 0% in the CEREBROLYSIN® (a mixture of neuropeptides derived from an enzymatic hydrolytic swine brain protein fraction and containing 15% of peptides with a molecular weight of 10,000 or less and approximately 85% of free amino acids including 3.00 mg alanine, 3.00 mg of aspartic acid, 0.06 g of cystine, 4.30 mg of glutamic acid, 1.50 mg of glycine, 1.30 mg of histidine, 2.00 mg of isoleucine, 6.00 mg of leucine, 0.50 mg of methionine, 2.00 mg of phenylalanine, 2.00 mg of proline, 0.30 g of serine, 0.30 g of threonine, 0.50 g of tryptophane and 2.00 mg of tyrosine) group, showing that CEREBROLYSIN® (a mixture of neuropeptides derived from an enzymatic hydrolytic swine brain protein fraction and containing 15% of peptides with a molecular weight of 10,000 or less and approximately 85% of free amino acids including 3.00 mg alanine, 3.00 mg of aspartic acid, 0.06 g of cystine, 4.30 mg of glutamic acid, 1.50 mg of glycine, 1.30 mg of histidine, 2.00 mg of isoleucine, 6.00 mg of leucine, 0.50 mg of methionine, 2.00 mg of phenylalanine, 2.00 mg of proline, 0.30 g of serine, 0.30 g of threonine, 0.50 g of tryptophane and 2.00 mg of tyrosine) therapy exerted a survival-enhancing effect in this disease (FIG. 1).

Animals were then killed by perfusion fixation and brains were removed, embedded in paraffin, cut sagitally and stained with luxol fast blue for testing vacuolisation in the white matter. FIG. 2 shows luxol fast blue and Nissl stained sagittal brain cut of a CADASIL mouse 0.5 mm laterally of the middle line. Cell body is dark blue; white matter imposes turquoise. The dashed line comprises the region observed, anterior corpus callosum.

Figures 3A, 3B:
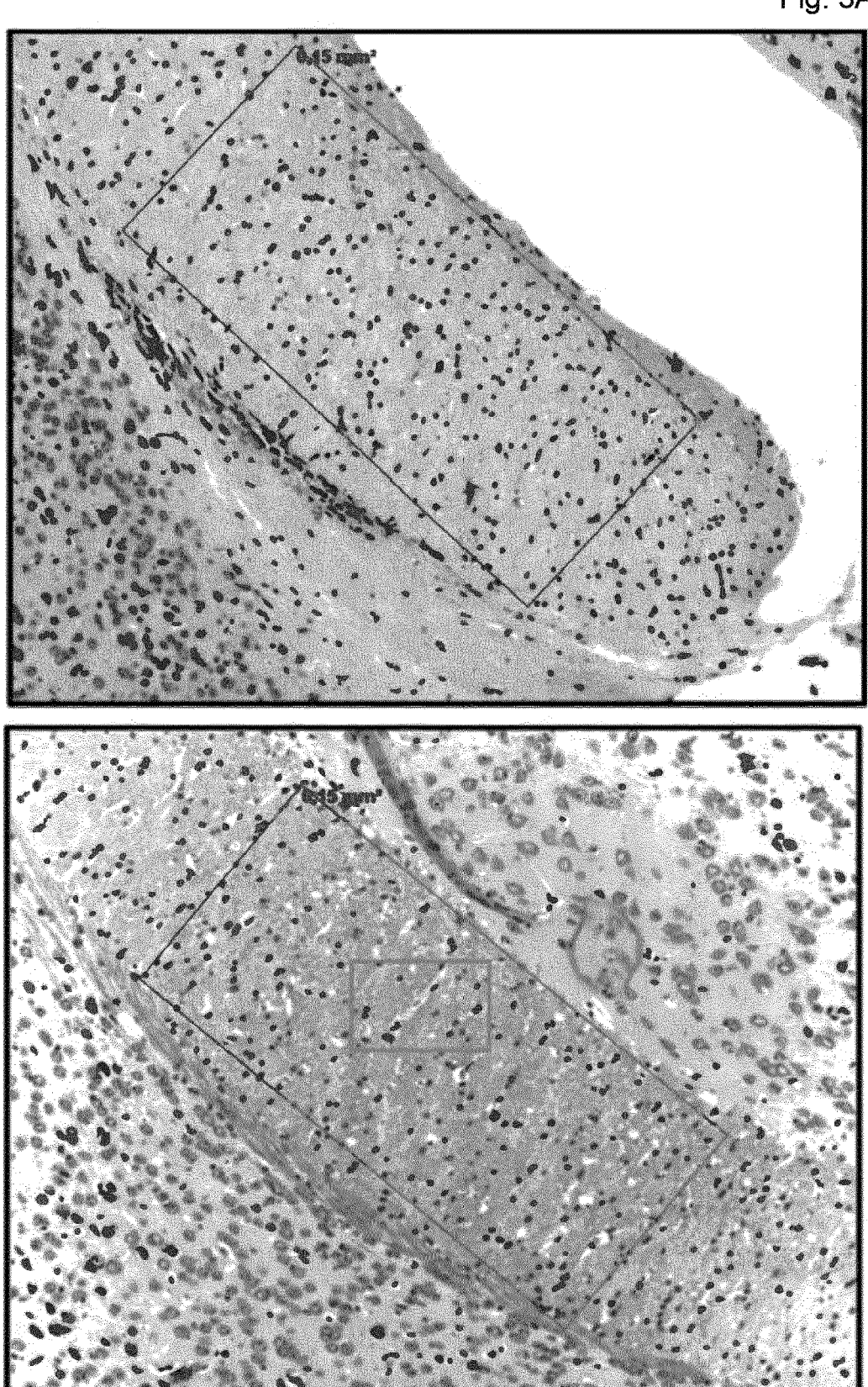

Six weeks old male C57BL/6 showed no vacuolation in the anterior medial corpus callosum (FIG. 3A), the structure which is pathologically altered in CADASIL mice (Joutel et al, J. Clin. Invest. 120 (2010), 433-445). In contrast, pronounced vacuolization was observed in CADASIL mice (FIG. 3B). Thus, it was possible to reproduce the pathological changes in the white matter of CADASIL mice known from the literature. In animals treated with the carrier substance, 22±7 vacuoles (mean±standard deviation, n=8) were measured, 26±5 vacuoles (n=14) in the animals treated with cerebrolysin). The differences between the groups are not significant (FIG. 4; p=0.12; Student t-test). In this respect, cerebrolysin appears to have no effect on the vacuolization of the white substance in CADASIL mice Taken together, the outstanding positive effect on mortality shows that cerebrolysin is a potent therapeutic agent candidate to combat CADASIL disease.

The invention claimed is:

1. A method of prolonging the lifespan of patients with cerebral autosomal dominant arteriopathy with subcortical infarcts and leukoencephalopathy (CADASIL) compared to corresponding CADASIL patients with no treatment, wherein the patients with CADASIL have a Notch3 gene mutation resulting in Notch3 aggregation, white matter damage, and reduced cerebral blood flow and modeled by transgenic mice expressing a human Notch3$^{R169C}$ gene, the method comprising:

obtaining a CEREBROLYSIN® preparation which contains 215.2 mg of CEREBROLYSIN® concentrate, wherein the CEREBROLYSIN® concentrate is a mixture of neuropeptides derived from an enzymatic hydrolytic swine brain protein fraction and containing 15% of peptides with a molecular weight of 10,000 or less and approximately 85% of free amino acids including 3.00 mg alanine, 3.00 mg of aspartic acid, 0.06 g of cystine, 4.30 mg of glutamic acid, 1.50 mg of glycine, 1.30 mg of histidine, 2.00 mg of isoleucine, 6.00 mg of leucine, 0.50 mg of methionine, 2.00 mg of phenylalanine, 2.00 mg of proline, 0.30 g of serine, 0.30 g of threonine, 0.50 g of tryptophane and 2.00 mg of tyrosine in 1 ml of the preparation; and administering the CEREBROLYSIN® preparation to the patients;

wherein the lifespan of patients with CADASIL is pro-
longed compared to the lifespan of corresponding
CADASIL patients with no treatment.

2. The method of claim 1, wherein the patients with
CADASIL are treated with a dose in a range of 0.1 to 100
ml of the CEREBROLYSIN® preparation corresponding to
21.5 to 21,520 mg of the CEREBROLYSIN® concentrate,
wherein the CEREBROLYSIN® concentrate is a mixture of
neuropeptides derived from an enzymatic hydrolytic swine
brain protein fraction and containing 15% of peptides with
a molecular weight of 10,000 or less and approximately 85%
of free amino acids including 3.00 mg alanine, 3.00 mg of
aspartic acid, 0.06 g of cystine, 4.30 mg of glutamic acid,
1.50 mg of glycine, 1.30 mg of histidine, 2.00 mg of
isoleucine, 6.00 mg of leucine, 0.50 mg of methionine, 2.00
mg of phenylalanine, 2.00 mg of proline, 0.30 g of serine,
0.30 g of threonine, 0.50 g of tryptophane and 2.00 mg of
tyrosine.

3. The method of claim 2, wherein the patients with
CADASIL are treated with a dose in a range 1 to 50 ml of
the CEREBROLYSIN® preparation.

4. The method of claim 1, wherein the patients with
CADASIL are treated with an intramuscularly administered
dose of 0.1 to 10 ml of the CEREBROLYSIN® preparation
corresponding to 21.5 mg to 2.152 mg of the CEREBROLY-
SIN® concentrate, wherein the CEREBROLYSIN® con-
centrate is a mixture of neuropeptides derived from an
enzymatic hydrolytic swine brain protein fraction and con-
taining 15% of peptides with a molecular weight of 10,000
or less and approximately 85% of free amino acids including
3.00 mg alanine, 3.00 mg of aspartic acid, 0.06 g of cystine,
4.30 mg of glutamic acid, 1.50 mg of glycine, 1.30 mg of
histidine, 2.00 mg of isoleucine, 6.00 mg of leucine, 0.50 mg
of methionine, 2.00 mg of phenylalanine, 2.00 mg of pro-
line, 0.30 g of serine, 0.30 g of threonine, 0.50 g of
tryptophane and 2.00 mg of tyrosine.

5. The method of claim 4, wherein the patients with
CADASIL are treated with an intramuscularly administered
dose of 0.5 to 5 ml of the CEREBROLYSIN® preparation.

6. The method of claim 1, wherein the patients with
CADASIL are treated with an intravenously administered
dose of 0.1 to 100 ml of the CEREBROLYSIN® preparation
corresponding to 215.2 to 21.520 mg of the CEREBROLY-
SIN® concentrate, wherein the CEREBROLYSIN® con-
centrate is a mixture of neuropeptides derived from an
enzymatic hydrolytic swine brain protein fraction and containing 15% of peptides with a molecular weight of 10,000
or less and approximately 85% of free amino acids including
3.00 mg alanine, 3.00 mg of aspartic acid, 0.06 g of cystine,
4.30 mg of glutamic acid, 1.50 mg of glycine, 1.30 mg of
histidine, 2.00 mg of isoleucine, 6.00 mg of leucine, 0.50 mg
of methionine, 2.00 mg of phenylalanine, 2.00 mg of pro-
line, 0.30 g of serine, 0.30 g of threonine, 0.50 g of
tryptophane and 2.00 mg of tyrosine.

7. The method of claim 1, wherein the patients with
CADASIL are treated with an intravenously administered
dose of 1 to 50 ml of the CEREBROLYSIN® preparation.

8. The method of claim 1, wherein the patients with
CADASIL are treated by continuously infusing the CERE-
BROLYSIN® preparation.

9. The method of claim 8, wherein infusion is performed
for an infusion duration of 5 min to 4 h and/or wherein
infusion is performed for from 1 day to 100 days.

10. The method of claim 9, wherein infusion is performed
for an infusion duration of 15 to 60 min and/or wherein
infusion is performed for from 10 to 30 days.

11. The method of claim 9, wherein infusion is performed
once per day.

12. The method of claim 1, wherein the CEREBROLY-
SIN® concentrate is diluted with 0.9% sodium chloride
solution, Ringer's solution, or 5% glucose, wherein the
CEREBROLYSIN® concentrate is a mixture of neuropep-
tides derived from an enzymatic hydrolytic swine brain
protein fraction and containing 15% of peptides with a
molecular weight of 10,000 or less and approximately 85%
of free amino acids including 3.00 mg alanine, 3.00 mg of
aspartic acid, 0.06 g of cystine, 4.30 mg of glutamic acid,
1.50 mg of glycine, 1.30 mg of histidine, 2.00 mg of
isoleucine, 6.00 mg of leucine, 0.50 mg of methionine, 2.00
mg of phenylalanine, 2.00 mg of proline, 0.30 g of serine,
0.30 g of threonine, 0.50 g of tryptophane and 2.00 mg of
tyrosine.

13. The method of claim 1, wherein the patients with
CADASIL are treated with the CEREBROLYSIN® prepa-
ration containing sodium hydroxide.

14. The method of claim 1, wherein the patients with
CADASIL are treated in treatment cycles which are repeated
after a treatment-free period of 1 to 6 months.

15. The method of claim 14, wherein the patients with
CADASIL are treated in treatment cycles which are repeated
after a treatment-free period of 2 to 3 months.

* * * * *